United States Patent [19]

Chandesais

[11] 4,351,584
[45] Sep. 28, 1982

[54] RING LIGHTING FOR MICROSCOPES

[76] Inventor: Jean L. Chandesais, Schawijkstraat 27, 2228 Ranst, Belgium

[21] Appl. No.: 135,770

[22] Filed: Mar. 31, 1980

[30] Foreign Application Priority Data

Apr. 11, 1979 [BE] Belgium ................................. 57718

[51] Int. Cl.³ ............................................. G02B 21/10
[52] U.S. Cl. ...................................................... 350/89
[58] Field of Search ................... 354/128, 23; 350/17, 350/35, 45, 87, 88, 89, 90; 250/356; 356/30; 63/32; 362/32

[56] References Cited

U.S. PATENT DOCUMENTS

| 1,427,714 | 8/1922 | Beck | 350/89 |
| 2,157,437 | 5/1939 | Shipley | 350/89 |
| 2,809,554 | 10/1957 | Bernhardt | 350/89 |
| 3,078,764 | 2/1963 | Barabas et al. | 350/89 |
| 3,752,560 | 8/1973 | Lunn | 350/89 |
| 3,920,311 | 11/1975 | Tsuda et al. | 350/89 |
| 3,930,713 | 1/1976 | Stakewitz et al. | 350/89 |
| 3,971,621 | 7/1976 | Albrecht-Buehler | 350/87 |
| 4,152,069 | 5/1979 | Bruck | 356/30 |
| 4,160,578 | 7/1979 | Gottlieb et al. | 350/89 |
| 4,259,011 | 3/1981 | Crumm et al. | 356/30 |
| 4,291,938 | 9/1981 | Wagner | 350/89 |

FOREIGN PATENT DOCUMENTS 1913711 3/1968 Fed. Rep. of Germany ........ 350/87

Primary Examiner—Jon W. Henry
Attorney, Agent, or Firm—Bacon & Thomas

[57] ABSTRACT

Improved ring lighting for microscopes, characterized in that it comprises substantially the combination of a light source remote from the precious stone being examined, a glass fiber guide extending to an annular endpiece and a reflector secured on the latter.

2 Claims, 6 Drawing Figures

RING LIGHTING FOR MICROSCOPES

BACKGROUND OF THE INVENTION

This invention relates to an improved ring lighting for microscopes, more particularly microscopes such as those used for examination, more particularly as regards the purity of precious stones.

It is known that such lighting for microscopes is extremely important since, for a good observation of the inclusions present in a precious stone, structural phenomena such like, and any hindering light effect among other things as a result of reflection on the polished facets of the precious stone must be avoided.

For this purpose, there has already been used for a long time a kind of lighting, more particularly a so-called dark ground lighting comprising substantially a lighting screened for the eye, a black background provided under the diamond so that the light is located on the side of the precious stone, thereby impinging the said precious stone from a direction which is more or less perpendicular to the observation direction.

The major drawback of said known dark ground lighting lies principally in that the light intensity thereof is too weak to allow an optimum observation.

It has also already been proposed to improve the light intensity, e.g. by using a lamp having a higher wattage, but other drawbacks result therefrom such as a too important heat evolution, a warm air stream along the precious stone, thereby forming heat vibrations hindering the observation around the precious stone, etc.

In order to prevent these last drawbacks, it has also already been suggested to use a lamp having a higher wattage with a suitable cooling system, but the drawback thereof lies in a very expensive device.

SUMMARY OF THE INVENTION

Thus, it is an object of the present invention to provide a ring lighting for the observation of a precious stone by means of a microscope while entirely excluding the aforesaid drawbacks and others in spite of the fact that the light intensity is substantially increased.

For this purpose, this ring lighting comprises substantially the combination of a source of light remote from the precious stone being examined, a fiberglass light conductor extending to an annular end-piece and a reflector secured on the latter.

BRIEF DESCRIPTION OF THE DRAWINGS

The characteristics of the improvements according to the invention will be more clearly pointed out hereafter by way of example and without any limitation through the following description of some preferred embodiments of a ring lighting according to the invention, reference being made to the enclosed drawings in which.

DESCRIPTION OF THE PREFERRED EMBODIMENTS

Figure 1:
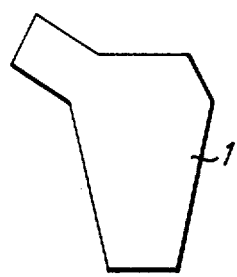
FIG. 1 is a diagrammatic view of a known so-called dark ground lighting.

FIG. 1 shows diagrammatically a known dark ground lighting, the microscope optics being indicated by 1, whereas the dark ground lighting proper is formed, e.g. by an annular lamp 2 which is disposed behind a screen 3 relative to the microscope optics 1, whereas a black background 5 is provided behind the precious stone 4 being examined, still relative to the microscope optics 1.

Such arrangement has the previously mentioned drawbacks.

Figure 2:
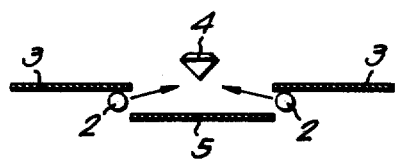
FIG. 2 shows a cross-section through a ring lighting according to the invention.
Figure 2:
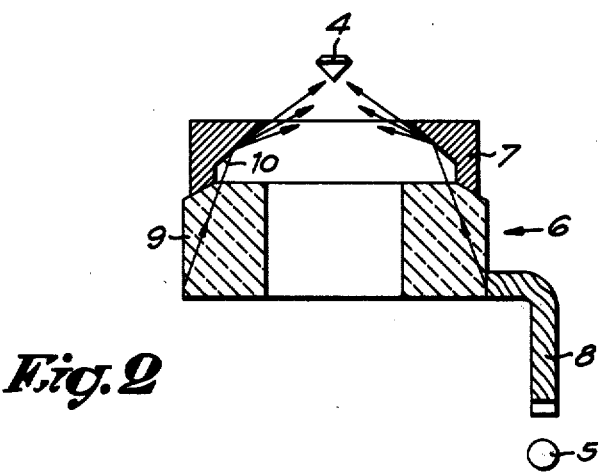

FIG. 2 shows the very simple ring lighting according to the invention, said lighting being mainly formed for the examination of a precious stone 4 by a separate source of light 5, a fiberglass light conductor 6 known per se and a reflector 7.

As it is known, the irradiated by the source of light 5 is collected by a bundle of glass fibres 8, the fibres of said bundle being suitably distributed in an annular end-piece 9 in order to transmit an annulus of light to the upper surface of said end-piece 9. The light irradiated through the end-piece 9 is then collected by the reflector 7 which is therefor provided with an internal conical surface 10 so that, by using a light source 5 having a high light intensity, a large amount of light is thereby projected onto the precious stone being examined, the light rays reflected by the reflector 7 being maintained as nearly horizontal as possible relative to the vertical observation direction of the precious stone 4 so that, by locating the source of light 5 at a suitable distance from the observation location, the heat evolved from said source has no influence on the observation.

In order to maintain the reflections on the polished facets of the precious stone at the lowest possible minimum, it will be preferable to maintain the surface 10 in a rough state, thereby providing a diffuse reflection. The material for this rough embodiment will be e.g. metal, synthetic material, but also, e.g. glass.

Figure 3:
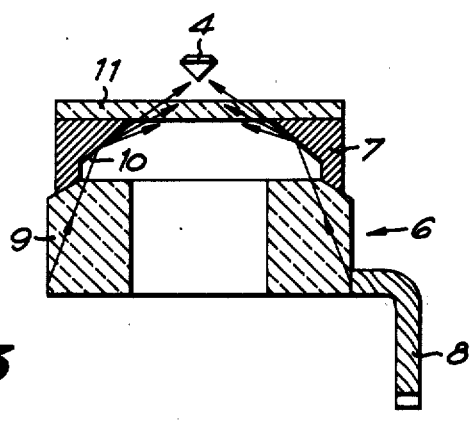
FIG. 3 shows a modified embodiment of FIG. 2.

This diffuse effect can be still increased by adapting a ground glass 11 above the reflector 7 as represented namely in FIG. 3.

Figure 4:
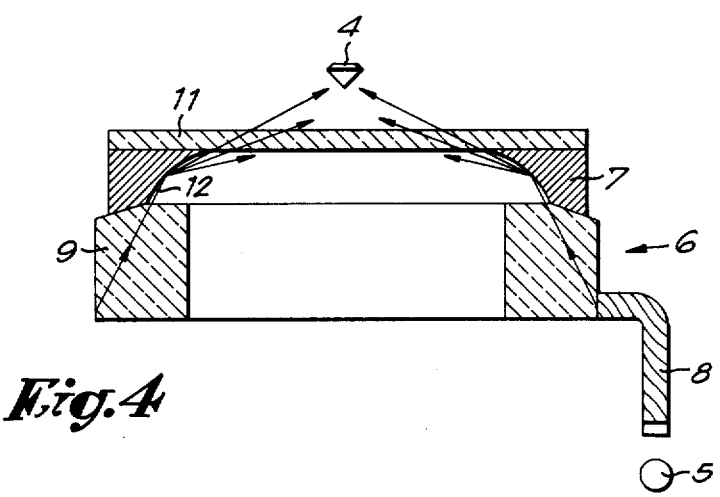
FIGS. 4, 5 and 6 show still other modified embodiments of a lighting according to the invention.
Figure 5:
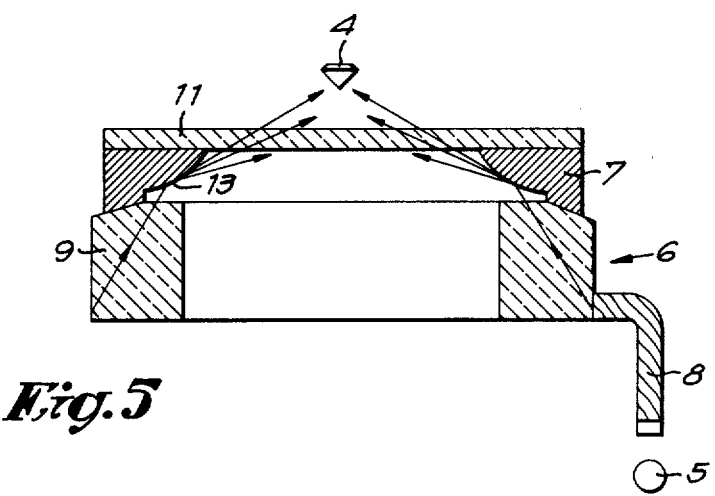
Figure 6:
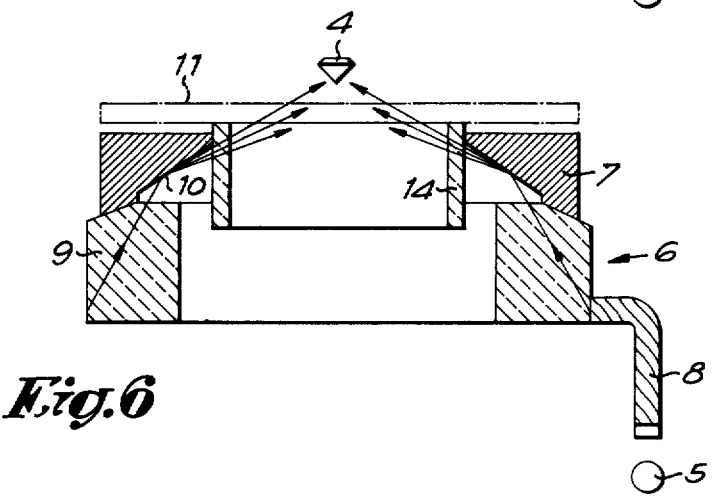

Finally, FIGS. 4, 5 and 6 show still three modified embodiments, the reflector 7 of FIG. 4 being provided with a concave annular surface 12 whereas the reflector 7 of FIG. 5 is formed by a convex annular surface 13, FIG. 6 showing an embodiment wherein an annular ground glass 14 is applied in the reflector 7 in combination or not with a ground glass 11.

It is apparent that the present invention is not at all limited to the embodiment described by way of example and illustrated in the attached drawings, but such ring lighting may be made in various combinations without departing from the scope of the invention.

What I claim is:

1. An illumination device for use in a microscope to illuminate, in a ring-shaped manner, a precious stone to be examined by said microscope along a viewing axis, said device including:
    a source of light mounted at a distance from said precious stone;
    a ring-shaped piece mounted around said viewing axis;
    a light conducting fiber arranged between said source of light and said annular light transmitter, said transmitter, when receiving light from said light source through said light conducting fibers spreading said light over an annular surface;
    an annular reflector mounted adjacent said ring-shaped piece and having a rough inner surface which is inclined with respect to said axis and which is adapted to reflect the light from said annular surface toward said viewing axis in a diffused way;

a ground glass applied within said annular reflector, between said reflector and said precious stone, whereby substantially all of the light reflected by the annular reflector strikes the ground glass.

2. An illumination device as defined in claim 1, which further includes another ground glass between said reflector and said precious stone.

* * * * *